United States Patent
Schneider et al.

(10) Patent No.: US 10,115,483 B2
(45) Date of Patent: *Oct. 30, 2018

(54) SYSTEM AND METHOD FOR CLINICAL ORDER RESCHEDULING

(71) Applicant: CERNER INNOVATION, INC., Kansas City, KS (US)

(72) Inventors: Charles Schneider, Trimble, MO (US); Britton Jennings, Smithville, MO (US); Elizabeth J. Parman, Overland Park, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 912 days.

This patent is subject to a terminal disclaimer.

(21) Appl. No.: 14/585,304

(22) Filed: Dec. 30, 2014

(65) Prior Publication Data

US 2015/0154376 A1   Jun. 4, 2015

Related U.S. Application Data

(63) Continuation of application No. 11/432,607, filed on May 11, 2006, now Pat. No. 10,049,186.

(51) Int. Cl.
*G06F 19/00* (2018.01)
*G06Q 50/22* (2018.01)
(Continued)

(52) U.S. Cl.
CPC ............ *G16H 20/10* (2018.01); *G06F 19/00* (2013.01); *G06F 19/3456* (2013.01); *G06Q 20/203* (2013.01); *G06Q 50/22* (2013.01); *H04L 67/10* (2013.01)

(58) Field of Classification Search
CPC ............... G06Q 50/24; G06Q 10/1093; G06Q 10/1095; G06F 19/3456; G06F 19/3462; G06F 19/00; G06F 19/3418; G06F 19/326; G06F 19/328; G06F 19/3481; G16H 10/60; G16H 20/10
See application file for complete search history.

(56) References Cited

U.S. PATENT DOCUMENTS

2004/0093252 A1   5/2004   Maekawa
2004/0193446 A1   9/2004   Mayer et al.
(Continued)

OTHER PUBLICATIONS

Non-Final Office Action dated Sep. 29, 2009 in U.S. Appl. No. 11/432,606, 8 pages.
(Continued)

*Primary Examiner* — Maroun P Kanaan
(74) *Attorney, Agent, or Firm* — Shook, Hardy & Bacon L.L.P.

(57) ABSTRACT

A system and associated methods are disclosed for generating alternative scheduling for orderable administration. In one embodiment, input is received regarding proposed timing for changing a current administration schedule for a substance-based orderable associated with an established order. Based on the input, one or more options for a revised administration schedule associated with the established order are generated. The generation of the scheduling options takes into consideration a policy for maintaining a degree of commonality with the current administration schedule.

15 Claims, 6 Drawing Sheets

(51) Int. Cl.
*H04L 29/08* (2006.01)
*G16H 20/10* (2018.01)
*G06Q 20/20* (2012.01)

(56) References Cited

U.S. PATENT DOCUMENTS

| | | | | |
|---|---|---|---|---|
| 2005/0021367 A1* | 1/2005 | Saeger | ............... | G06F 19/3456 705/2 |
| 2005/0234741 A1* | 10/2005 | Rana | ................... | G06Q 10/107 705/2 |
| 2006/0010009 A1 | 1/2006 | Fangman | | |
| 2006/0265245 A1* | 11/2006 | McCallie | ............ | G06F 19/3456 705/2 |

OTHER PUBLICATIONS

Final Office Action dated Apr. 13, 2010 in U.S. Appl. No. 11/432,606, 9 pages.
Notice of Allowance dated Jan. 19, 2011 in U.S. Appl. No. 11/432,606, 57 pages.
Second Notice of Allowance dated May 17, 2011 in U.S. Appl. No. 11/432,606, 5 pages.
Non-Final Office Action dated Oct. 6, 2009 in U.S. Appl. No. 11/432,607, 11 pages.
Final Office Action dated Jun. 8, 2010 in U.S. Appl. No. 11/432,607, 11 pages.
Supplemental Final Office Action dated Aug. 12, 2010 in U.S. Appl. No. 11/432,607, 11 pages.
Notice of Allowance dated May 23, 2014 in U.S. Appl. No. 11/432,607, 9 pages.
Non-Final Office Action dated Aug. 7, 2014 in U.S. Appl. No. 11/432,607, 4 pages.
Final Office Action dated Feb. 26, 2015 in U.S. Appl. No. 11/432,607, 5 pages.
Notice of Allowance dated Dec. 18, 2017, in U.S. Appl. No. 11/432,607, 10 pages.

* cited by examiner

SYSTEM AND METHOD FOR CLINICAL ORDER RESCHEDULING

CROSS-REFERENCE TO RELATED APPLICATIONS

This application is a continuation of and claims priority to U.S. patent application Ser. No. 11/432,607, filed May 11, 2006 and titled "System and Method for Clinical Order Rescheduling", the disclosure of which is incorporated by reference herein in its entirety.

BACKGROUND

Providers of healthcare services, such as clinicians, prescribe or recommend various orderables to treat ailments or conditions diagnosed in patients. Examples of categories of orderables include substance-based agents (such as medications or other chemical agents), medical equipment, supplies, laboratory tests, or medical services. Increasingly, clinicians are utilizing electronic order management systems to enter and manage orderables for their patients. One example of such an electronic order management system is the POWERORDERS application available from Cerner Corporation of North Kansas City, Mo. For instance, using such an order management system, a physician or other clinician wishing to prescribe a medication for a particular patient may access a profile for the patient and initiate an order for the medication, entering details for the medication order. After initiating the order, the physician may "sign" the order, indicating to the order management system to process the order. Once the order has been processing in the order management system, it is electronically dispersed to the appropriate location, such as a pharmacy. In addition, the order is maintained in the profile, which allows other clinicians to view the order as well as other orders that have been placed for the patient.

Orders for substance-based orderables may be created by a clinician for administration of the medication or chemical agent to a patient on an "as needed" or P.R.N. basis, or alternatively, on a scheduled basis. As illustrative examples of scheduled orderables, a physician may prescribe an antibiotic to be taken once or twice a day for a certain number of days to treat an infection, or a chemotherapy agent to be taken over a period of time to kill cancerous cells. One difficulty with scheduled orderables is how to compensate when a dose is not administered at the time scheduled. A clinician may have created a B.I.D. order schedule (twice-a-day administration) so that a medication is received, for instance, around the time a hospitalized patient eats their morning and evening meals. If another clinician or aide fails to administer the medication dose at the scheduled time (or administers the medication too soon), future scheduled administration times may need to be altered to ensure the patient receives the therapeutic effect from the medication that was intended by the prescribing clinician.

However, with certain medications or chemical agents, and sometimes dependant upon the conditions they are intended to treat, altering an administration schedule for these substance-based orderables can have significant negative consequences for the patient. For instance, if a scheduled administration of a chemotherapy agent is missed, or a patient must alter the time of the day they normally receive a chemotherapy dose, it may or may not be prudent (e.g., according to a standard of care protocol) to administer the dose immediately when it is noticed that the scheduled time has passed or a new scheduled time has arisen. Additionally, these changes may alter the total length of time for the order, which may be undesirable if the substance-based orderable (such as a chemotherapy agent) is only supposed to be present within the patient's body for a set period of time.

The difficulty in altering administration schedules for substance-based orders is further complicated since a scheduling for an order may be altered in a number of ways, only some of which present a strong opportunity for maintaining the originally intended therapeutic effect for the patient. It can be difficult for clinicians to consider all of the scheduling options simultaneously. Specifically, it is difficult to easily comprehend how the schedule for administration of orderables compares across the revised scheduling options, and what particular variations from the originally intended administration schedule result if a particular revised scheduling option is selected.

BRIEF SUMMARY

A system and associated methods of the present invention enable the generation and presentation of scheduling options for a clinical order. In particular, certain embodiments focus on alternative scheduling for the administration of orderables to a patient in association with an established or preexisting clinical order.

In one aspect, a computerized method is provided for generating alternative scheduling for orderable administration. According to the method, input is received regarding proposed timing for changing a current administration schedule for a substance-based orderable associated with an established order. Based on the input, one or more options for a revised administration schedule associated with the established order are generated. The revised administration schedule options include a next administration for the substance-based orderable and a corresponding remaining administration schedule. Additionally, the generation of the scheduling options takes into consideration a policy for maintaining a degree of commonality with the current administration schedule. Thereafter, a graphical representation of the one or more scheduling options is displayed to provide a clinician the ability to review the parameters of the generated scheduling options.

In another aspect, a computerized method for generating alternative scheduling for orderable administration utilizes certain policies in establishing one or more options for a revised administration schedule. More specifically, the method includes receiving input regarding proposed timing for changing a current administration schedule associated with a established order, and thereafter determining one or more options for a revised administration schedule associated with the established order, each of the options being associated with one of the policies. The policies may include: (a) maintaining the remaining number of doses of the substance-based orderable to be administered under the current administration schedule associated with the established order; (b) maintaining the remaining number of doses of the substance-based orderable to be administered under the current administration schedule associated with the established order while observing a stop date and time for administration of the substance-based orderable that is as close as possible to a current stop date and time under the current administration schedule associated with the established order; and (c) observing a stop date and time for administration of the substance-based orderable that represents temporal proximity with a stop date and time under the current administration schedule associated with the established order.

The system and associated methods of the present invention provide an indication of the time-based parameters surrounding individual scheduling options for orderables, enabling a clinician to quickly contrast the scheduling options and determine which option presents the best opportunity for treating the particular patient's condition and achieving positive health outcomes.

Additional advantages and features of the invention will be set forth in part in a description which follows, and in part will become apparent to those skilled in the art upon examination of the following, or may be learned by practice of the invention.

BRIEF DESCRIPTION OF THE SEVERAL VIEWS OF THE DRAWING

The present invention is described in detail below with reference to the attached drawing figures, wherein.

DETAILED DESCRIPTION

Embodiments of the present invention relate to the establishment of scheduling options to modify administration times associated with an existing clinical order. Specifically, certain embodiments are concerned with substance-based orderables, such as medications and other chemical agents that are taken by a patient on a scheduled basis for a desired therapeutic effect and are thus described for explanation purposes in the context of doses or dosage administration. The modified or revised administration schedule options accounts for certain policies relating to a goal of maintaining some of the characteristics of a current administration schedule for an orderable. For instance, these policies may include maintaining the remaining number of orderable doses in the current administration schedule and/or observing an orderable administration stop date and time that is temporally proximal with a current stop date and time of the current administration schedule. In one embodiment, the revised administration schedule options are presented in a graphical display along with the current administration schedule, and may be plotted over a timeline as display objects representing specific times for administration of the orderable under the respective administration schedule. Additionally, the schedule options may be selectable to associate the desired administration schedule with the existing clinical order.

General Computing System Environment

Figure 1:
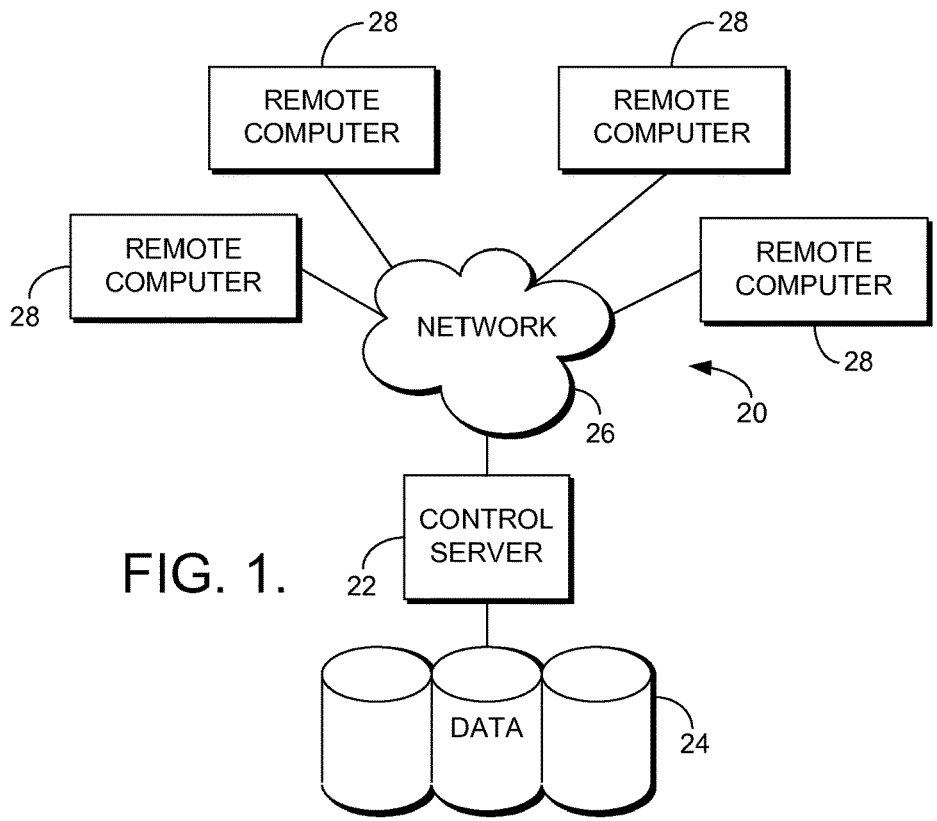
FIG. 1 is a block diagram of an exemplary computing system environment suitable for use in implementing the present invention.

Referring to the drawings in general, and initially to FIG. 1 in particular, an example of a suitable computing system environment in which the invention may be implemented, for instance, a medical information computing system, is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by control server 22, and includes volatile and nonvolatile media, as well as removable and nonremovable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage device, or any other medium which can be used to store the desired information and which may be accessed by control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for control server 22.

The control server 22 may operate in a computer network 26 using logical connections to one or more remote computers 28. Remote computers 28 may be located at a variety of locations in a medical environment or research environment, for example, but not limited to, clinical laboratories, hospitals and other inpatient settings, veterinary environments, ambulatory settings, medical billing and financial offices, administration settings, home health care environments, clinicians' offices, or any other healthcare provider or administrative settings. Clinicians, as referred to herein, may include, but are not limited to, a treating physician or physicians, specialists such as surgeons, radiologists and cardiologists, emergency medical technicians, physicians' assistants, nurse practitioners, nurses, nurses' aides, pharmacists, dieticians, microbiologists, laboratory experts, genetic counselors, researchers, veterinarians, students, and the like, and aides or assistants thereto. Remote computers 28 may also be physically located in non-traditional medical care environments so that the entire health care community may be capable of integration on the network. Remote computers 28 may be personal computers, servers, routers, network PCs, personal digital assistants (PDA), peer devices, other common network nodes, or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or all of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. The control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Scheduling Options Generation

As referenced above, embodiments of the present invention enable alternative scheduling options for an existing clinical order to be created. In embodiments, the scheduling options are designed to maintain the therapeutic effect delivered by an orderable according to an existing administration schedule when circumstances dictate a departure from the existing schedule such as a change in the time of administration on a unit-time basis (e.g., per day, per week, etc).

Figure 2:
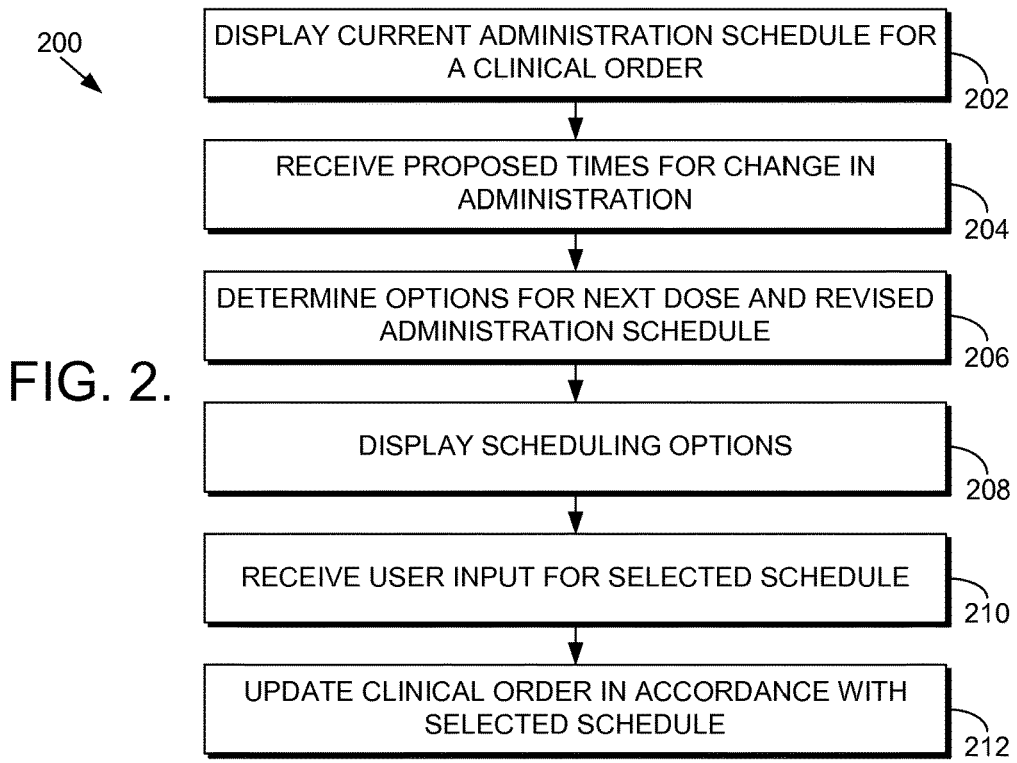
FIG. 2 depicts a flow diagram representative of one method for presenting options for orderable administration schedules as alternatives to a current orderable administration schedule and updating an order according to the option selected.

Turning now to FIG. 2, a flow diagram representative of a computerized method for establishing selectable options for orderable administration schedules is depicted generally as reference numeral 200. Initially, as shown at block 202 of FIG. 2, a current orderable administration schedule associated with an existing clinical order is displayed. By way of example, the administration schedule may be for a substance-based orderable to be taken by a patient (orally or intravenously, for instance) at certain time intervals per day, for a certain number of days. The associated clinical order may have been previously entered on an electronic order management system, or the like. At block 204, input is received regarding proposed times for a change in the administration schedule for the orderable. The input may include an earliest time for administering a dose on a unit-time basis (e.g., first dose of the day at 6:00 AM) and the number of doses to be administered per unit-time (e.g., twice a day, at regular intervals). Alternatively, the input may include a set of times for administration (e.g., 6:00 AM, 12:00 PM, etc.).

As previously mentioned, a variety of reasons may necessitate changing the timing for administration to properly deliver the care or therapeutic benefit intended by the clinician creating the existing order schedule. Sometimes a patient will receive a dose of the orderable at the wrong time on the administration schedule for the order, or changes in the health status of the patient or healthcare provider resources may dictate that orderable administration must be undertaken at different time intervals or at a different time of the day. It should be appreciated that a variety of other clinically relevant reasons may also necessitate the changing the orderable administration schedule.

The input regarding the proposed times can be utilized, at block 206, in determining options for a next administration timing and corresponding revised administration schedule for the orderable. In general, these options implement a policy that seeks to maintain a degree of commonality with the current administration schedule for the existing order, by, for instance, maintaining the remaining number of orderable doses in the current administration schedule and/or observing an orderable administration stop date and time that is temporally proximal with a current stop date and time associated with the current administration schedule. Once these revised administration scheduling options (including the timing for the next dosage administration) are determined, then at block 208, the scheduling options are displayed on a user interface. The display may involve both a graphical representation of the revised administration schedule options (e.g., plotted over a timeline) and a textual representation of the policy associated with each of the options. Each scheduling option may be represented graphically through a set of display objects representing specific times for administration of the orderable under the respective administration schedule.

Thereafter, at block 210, user input regarding a selection of one of the revised administration schedule options is received. Based on the particular selection, at block 212, the existing clinical order is updated in accordance with the selected schedule. Thus, in the electronic order management system, the selected administration schedule for the existing order includes, for instance, a new next dose administration date and time, a new stop date and time for orderable administration, and optionally, a change in the number of doses to be administered per unit-time. Additionally, if the original start date and time for the clinical order has not yet occurred (i.e., the order was entered into the electronic order management system, but with a future start date and time for orderable administration), the selected administration schedule also includes a new start data and time for orderable administration.

Figure 3A:
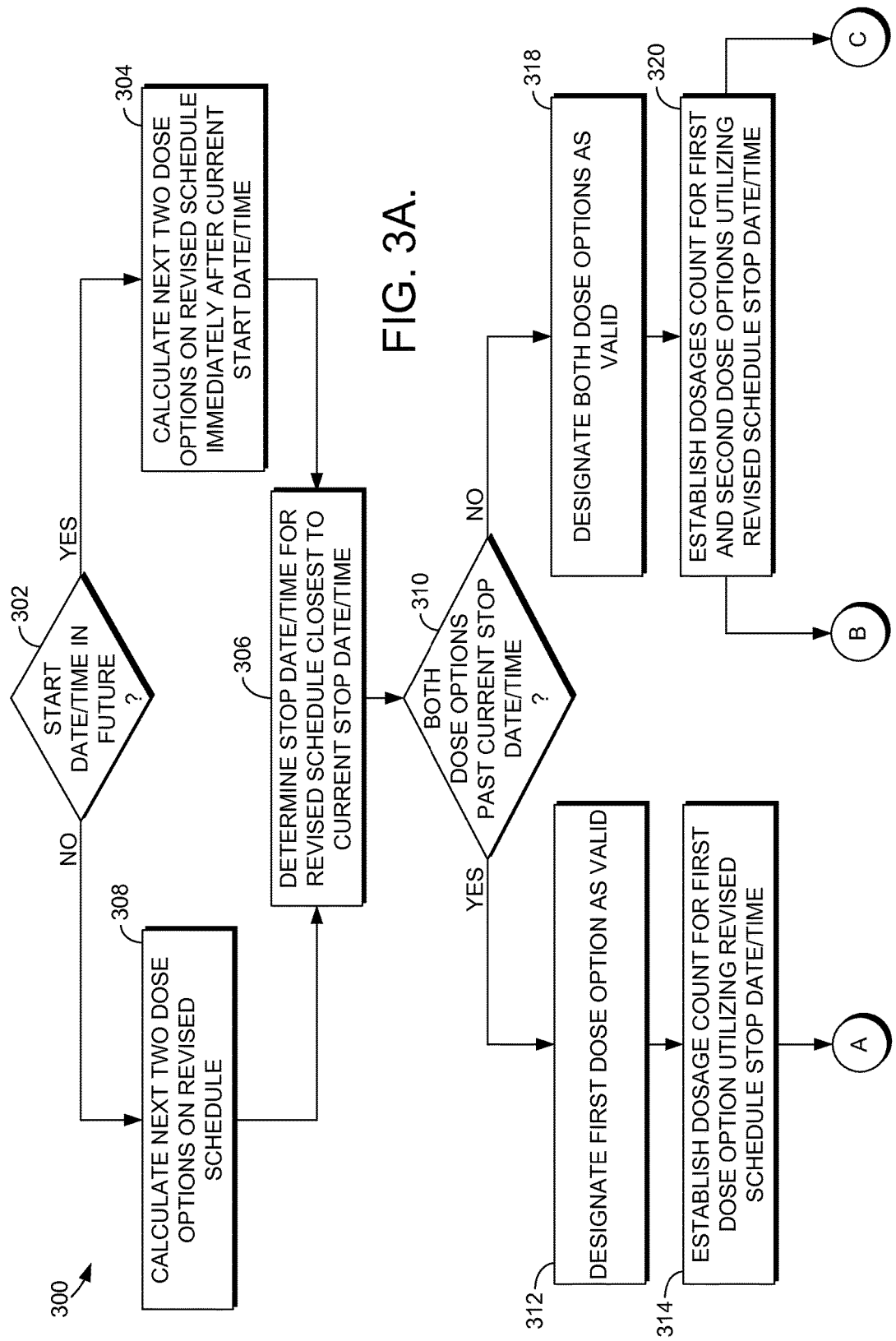
FIGS. 3A, 3B and 3C depict a flow diagram representative of one process for establishing one or more next dose options and associated revised orderable administration schedules.
Figure 3B:
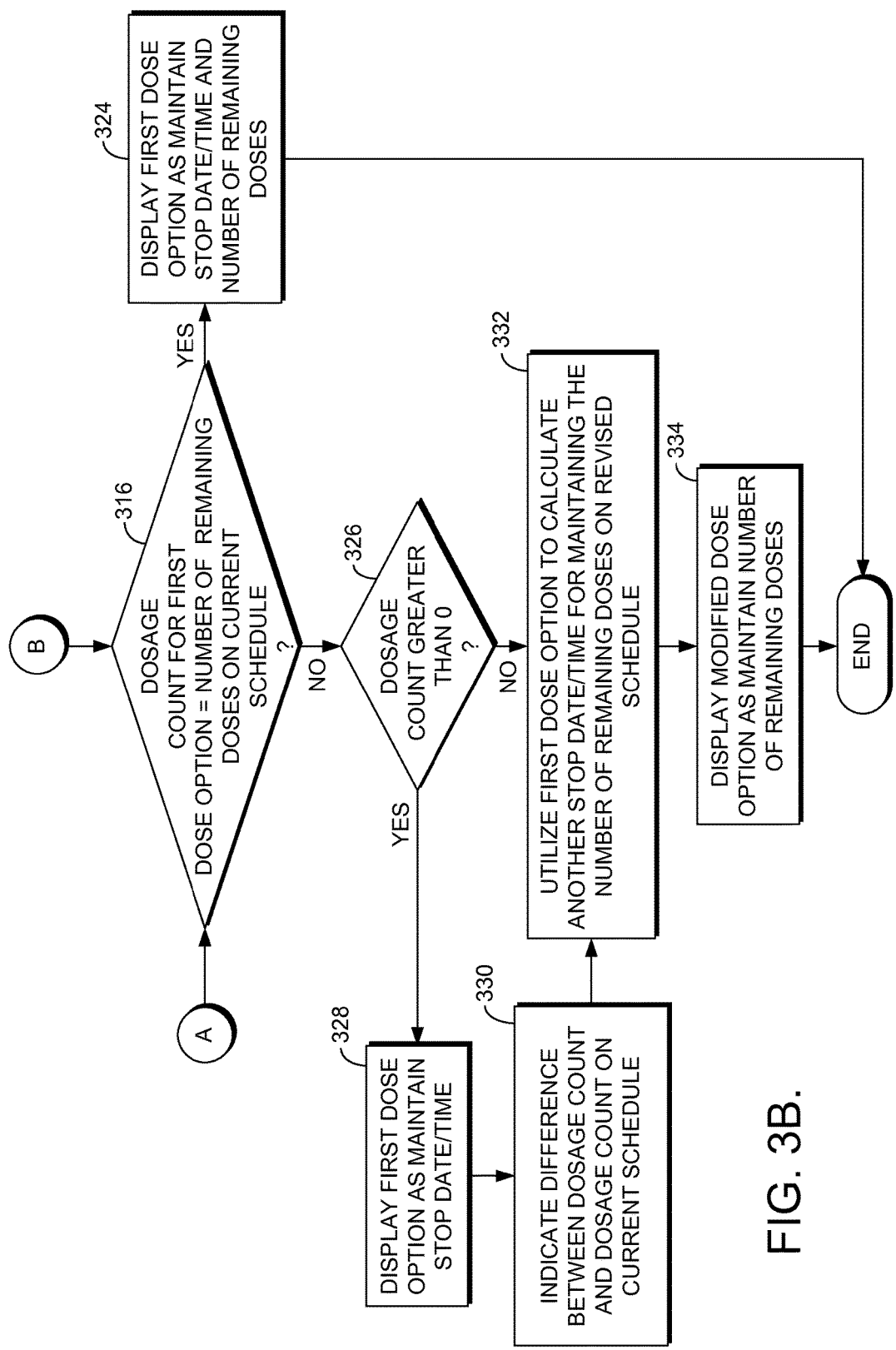
Figure 3C:
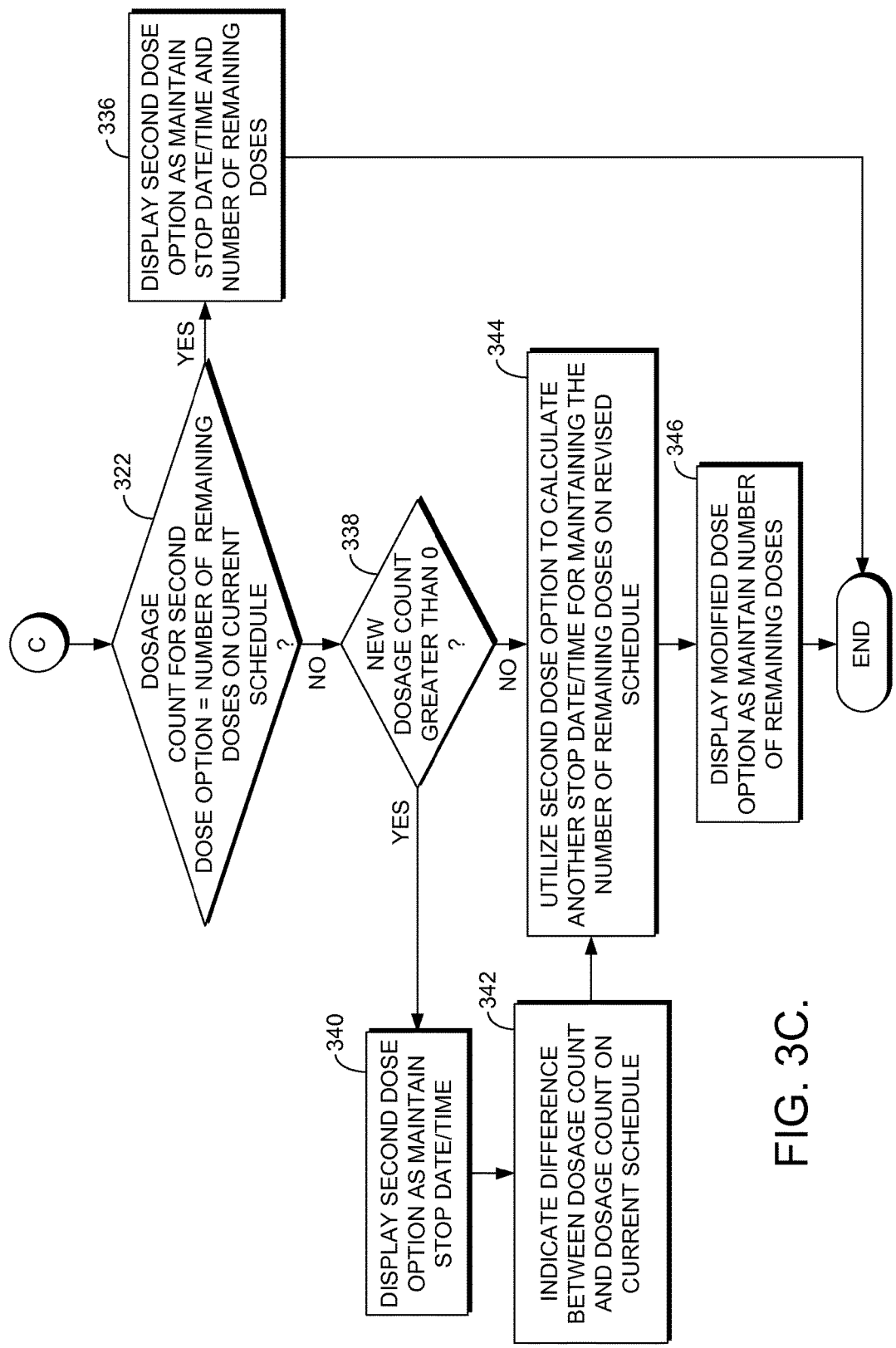

The determination of options at step 206 for a revised orderable administration schedule involves an underlying process 300 illustrated in FIGS. 3A-3C. Specifically, process 300 utilizes certain parameters surrounding the current administration schedule for the existing order to derive the new scheduling options for substance-based orderables. Beginning with block 302, the current administration schedule for an orderable is examined to determine if the corresponding start date and time for the schedule is in the future. If the start date and time for the current administration schedule is in the future, then at block 304, the next two dose options for a revised schedule that fall immediately after the start date and time for the current administration schedule are calculated, based on the input regarding proposed times for a change in the administration schedule. Thereafter, the process proceeds to block 306. Alternatively, if the start date and time for the current administration schedule has already passed, then at block 308, the next two dose options for a revised schedule that fall immediately after the current date and time (regardless of the current administration schedule) are calculated based on the input regarding the proposed times for changing the administration schedule. Thereafter, the process continues at block 306.

As an illustrative example, suppose the current time is "8:00 PM", the current administration schedule has a start date/time of "7:00 AM, Day 1" for an orderable administered generally every twelve hours+/−two hours (B.I.D.), and the input received indicates proposed timing for administration as "9:00 AM, 10:00 PM, Daily". Accordingly, the first dose option of the next two dose options may include a next administration time of "10:00 PM, Day 0", with the remaining administration schedule for the first dose option built off of this particular next dosage time. On the other hand, the second dose option of the next two dose options may include a next administration time of "9:00 AM, Day 1", with the remaining administration schedule for the second dose option built off of this particular next dosage time.

Returning to block 306, the new stop date and time for the revised administration schedule options (i.e., next two dose options) closest to the current administration schedule stop date and time are determined utilizing the frequency of orderable administration gleaned from the proposed times input. At block 310, it is determined whether each of the next two dose options for the revised administration schedule present an associated stop date and time that is past the current administration schedule stop date and time. If the next two dose options each present an associated stop date and time that is past the current administration schedule stop date and time, then at block 312, the first dose options is designated as a valid option and the dosage count for the first dose option is established at block 314 utilizing the stop date and time for the revised administration schedule associated with the first dose option. Thereafter, the process proceeds to block 316 of FIG. 3B.

Alternatively, at block 310, if at least one of the next two dose options for the revised administration schedule presents an associated stop date and time that is prior in time to the current administration schedule stop date and time, then at block 318, both of the first and second dose options are designated as valid options and the corresponding dosage count for each dose option is established at block 320 utilizing the stop date and time for the revised administration schedules associated with the first and second dose options. The process continues at block 316 of FIG. 3B for the first dose option and at block 322 of FIG. 3C for the second dose option.

With reference to FIG. 3B, at block 316, it is determined whether the dosage count for the first dose option is equal to the number of remaining doses on the current administration schedule. In the case where the dosage count for the first dose option is equal to the number of remaining doses on the current administration schedule, then at block 324, the first dose option is displayed as the scheduling option that maintains the remaining number of orderable doses in the current administration schedule while observing an orderable administration schedule stop date and time that is temporally proximal with a current stop date and time associated with the current administration schedule. For instance, in the previous example in which the current administration schedule has a start date/time of "7:00 AM, Day 1" for an orderable administered generally every twelve hours+/−two hours (B.I.D.), and utilizing a stop date and time of "9:00 PM, Day 3", if the first dose option presents timing for administration at "9:00 AM, 10:00 PM, Daily", then to maintain a degree of temporal proximity for the stop date and time (in one example, the closest possible time), the stop date and time for the revised schedule should be "10:00 PM, Day 3" instead of "9:00 AM Day 3 or Day 4". Subsequent to block 324, the process reaches an endpoint shown on FIG. 3B.

Alternatively, at block 316, if the dosage count for the first dose option is not equal to the number of remaining doses on the current administration schedule, then whether the dosage count for the first dose option is greater than zero is determined at block 326. A situation where the dosage count is greater than zero causes the first dose option to be displayed as the scheduling option that observes an orderable administration schedule stop date and time that is temporally proximal with a current stop date and time associated with the current administration schedule, at block 328. The difference between the dosage count for the first dose option and the dosage count for the remaining portion (i.e., the remaining doses) of the current administration schedule is indicated at block 330. Thereafter, the process moves to block 332. Returning to block 326, in a situation where the dosage count is equal to zero, on the other hand, the process moves directly to block 332.

The first dose option is utilized at block 332 to calculate another stop date and time for the revised administration schedule where the dosage count for the first dose option (as modified) would be a number equal to the number of remaining orderable doses in the current administration schedule. Thereafter, at block 334, the modified first dose option is displayed as the scheduling option that maintains the remaining number of orderable doses in the current administration schedule. The process then reaches the endpoint shown on FIG. 3B.

In FIG. 3C, the steps of process 300 represented perform the same function as the steps of process 300 represented in FIG. 3B, except that the portion of process 300 depicted in FIG. 3C is concerned with the second dose option as opposed to the first dose option in FIG. 3B. Turing to block 322, it is determined whether the dosage count for the second dose option is equal to the number of remaining doses on the current administration schedule. In the case where the dosage count for the second dose option is equal to the number of remaining doses on the current administration schedule, then at block 336, the second dose option for an orderable administration schedule is displayed as the scheduling option that maintains the remaining number of orderable doses in the current administration schedule while observing an orderable administration schedule stop date and time that is temporally proximal with a current stop date and time associated with the current administration schedule. Subsequent to block 336, the process reaches an endpoint shown on FIG. 3C.

Alternatively, at block 322, if the dosage count for the second dose option is not equal to the number of remaining doses on the current administration schedule, then whether the dosage count for the second dose option is greater than zero is determined at block 338. A situation where the dosage count is greater than zero causes the second dose option to be displayed as the scheduling option that observes an orderable administration schedule stop date and time that is temporally proximal with a current stop date and time associated with the current administration schedule, at block 340. The difference between the dosage count for the second dose option and the dosage count for the remaining portion of the current administration schedule is indicated at block 342. Thereafter, the process moves to block 344. Returning to block 338, in a situation where the dosage count is equal to zero, on the other hand, the process moves directly to block 344.

The second dose option is utilized at block 344 to calculate another stop date and time for the revised administration schedule where the dosage count for the second dose option (as modified) would be a number equal to the number of remaining orderable doses in the current administration schedule. Thereafter, at block 346, the modified second dose option is displayed as the scheduling option that maintains the remaining number of orderable doses in the current administration schedule. The process then reaches the endpoint shown on FIG. 3C.

Figure 4:
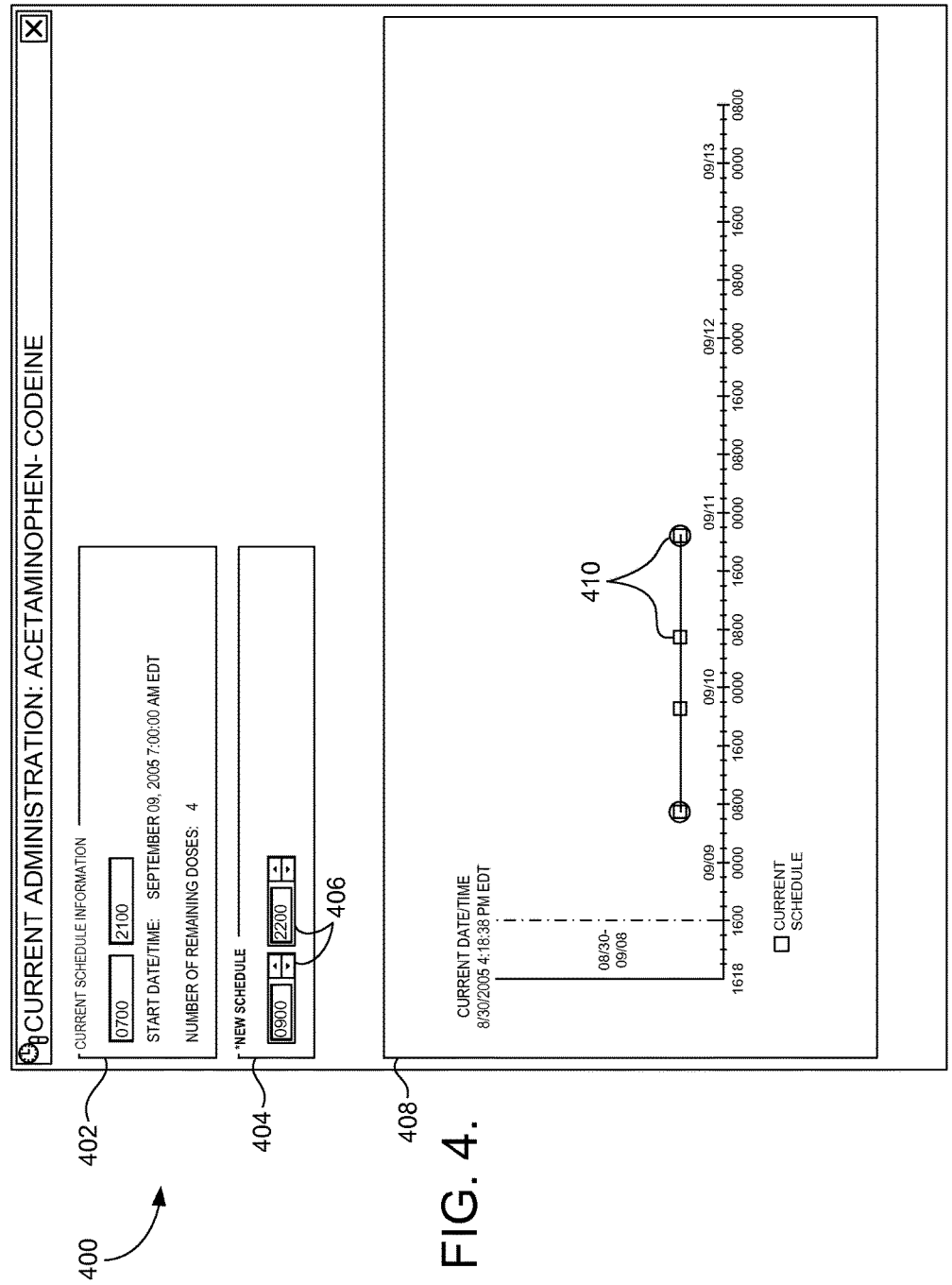
FIG. 4 is an exemplary screen display showing a graphical representation of a current orderable administration schedule and a dosage time selection area.

One exemplary screen display 400 showing the presentation of a current orderable administration schedule for an existing order is illustrated in FIG. 4. The screen display 400 has a first region 402 where current administration schedule information is provided, such as the daily times for administration of the listed substance-based orderable (e.g., Acetaminophen with Codeine), the start date and time for the existing order, and the number of remaining doses for the current schedule. In a second region 404, dosage time selectors 406 enable a user to input desired times for administration so that alternative scheduling for orderable administration may be generated. In one embodiment, the number of dosage time selectors 406 is equal to the number of current orderable administrations per-unit time under the current administration schedule. Therefore, if existing order is valid for administration twice a day, then two dosage time selectors 406 are presented. In an alternative embodiment, one dosage time selector may be presented along with a selector for the number of doses per unit time, so that the user can enter an earliest orderable administration time per unit time (e.g., first daily dose) along with a quantity of doses to be administered at regular intervals. Shown in a third region 408 is a graphical plotting of a set of display objects 410 on a timeline. Each display object 410 represents an orderable administration date and time under the current administration schedule.

Figure 5:
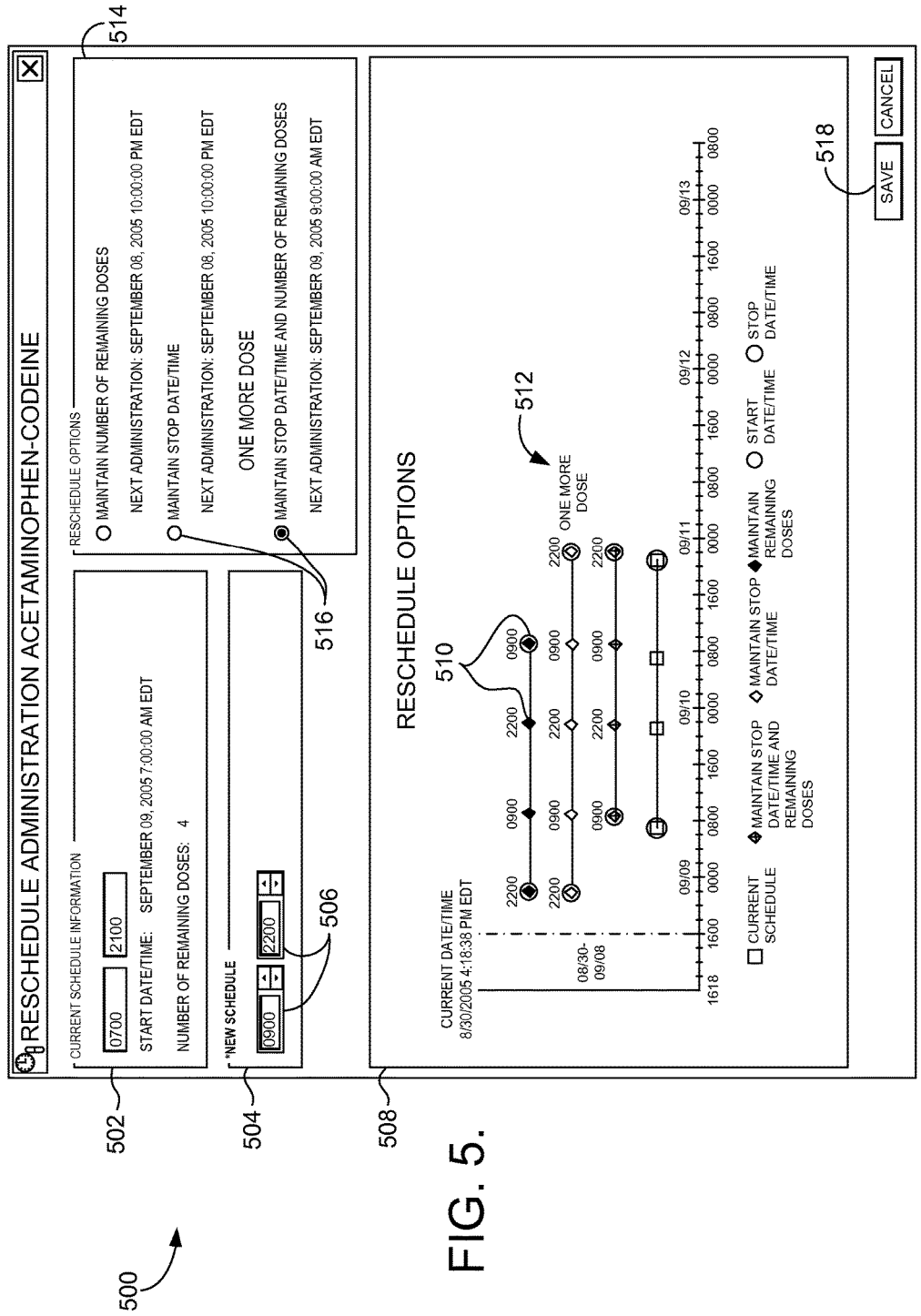
FIG. 5 is an exemplary screen display showing a graphical representation of current and proposed orderable administration schedules based on input received in the dosage time selection area.

Another exemplary screen display 500 is illustrated in FIG. 5. Screen display 500 presents the current orderable administration schedule for an existing order along with options for revised medication administration schedules based on the input to a set of dosage time selectors 506. In additional to a first display region 502 providing current administration schedule information, and a second display region 504 where the dosage time selectors 506 are disposed, a third display region 508 includes a graphical plotting of sets of display objects 510 for the current administration schedule as well as the options for revised administration schedules. As with the display objects 410 of FIG. 4, the display objects 510 represent orderable administration dates and times for the respective administration schedule. In the case where one option for an administration schedule is keeping with the policy of observing an orderable administration schedule stop date and time that is temporally proximal with a current stop date and time associated with the current administration schedule, a notification 512 is provided that the associated schedule option provides for one additional dosage of the orderable as compared to the number of remaining doses on the current administration schedule. A fourth display region 514 of the screen display 500 includes textual representations of the policy associated with each of the options for a revised administration schedule. Option selectors 516 are located in proximity to each of the textual representations, such that a user may select a particular selector 516 associated with one of the options for a revised administration schedule. Thereafter, a "Save" button 518 can be selected to update the existing clinical order according to the selector 516 chosen, to substitute the selected administration schedule option for the current administration schedule.

From the foregoing, it can be seen that the system and methods of the present invention provide for scheduling options when administration times under an existing order are to be modified. These scheduling options may be configured to take into account certain policies relating to a goal of maintaining some of the characteristics of a current administration schedule for an orderable. Additionally, graphical representations of the scheduling options may be presented along with the current administration schedule, enabling a clinician to quickly appreciate the differences between scheduling options.

The aforementioned system and methods have been described in relation to particular embodiments, which are intended in all respects to be illustrative rather than restrictive. Since certain changes may be made in the aforementioned system and methods without departing from the scope hereof, it is intended that all matter contained in the above description or shown in the accompanying drawing be interpreted as illustrative and not in a limiting sense.

What is claimed is:

1. An electronic order management system comprising:
a control server having a processing unit and internal system memory configured to:
receive a plurality of clinical substance-based orderables, each orderable associated with an established order and comprising a dose, a dose per unit time, and a number of doses per unit time;
receive an indication of a clinician input comprising more than one of a current administration schedule, a new administration schedule, or a reschedule administration option with regard to one of the plurality of clinical substance-based orderables associated with the established order;
generate options for a next administration of the one of the plurality of clinical substance-based orderables using the more than one of the current administration schedule, the new administration schedule, or the reschedule administration option, wherein the options generated for the next administration at least:
maintain the administration stop date and time in the current administration schedule for the one clinical substance-based orderable independent of the number of remaining doses of the one clinical substance-based orderable, or
maintain the remaining number of doses of the one clinical substance-based orderable in the current administration schedule and maintain the administration stop date and time in the current administration schedule for the one clinical substance-based orderable; and
causing the two or more of the options for the next administration to be concurrently displayed as selectable options via graphical user interface (GUI), the two or more options represented graphically as display objects representing specific times for the next administration under two or more of the current administration schedule, the new administration schedule, or the reschedule administration option.

2. The system of claim 1, wherein each of the plurality of clinical substance-based orderables includes a medication or a non-medication chemical agent.

3. The system of claim 1, wherein, in response to communication of the options for the next administration, the control server is further configured to receive an indication of a clinician selection comprising one or more of an earliest time for administering a dose and a number of doses per day of the substance-based orderable or a set of times representing when a dose of the substance-based orderable is to be administered within a day.

4. The system of claim 1, wherein the indication of a clinician selection further comprises a revised administration option such that the control server is further configured to update the established order based on the clinician selection of the revised administration schedule option.

5. The system of claim 4, wherein the control server is further configured to, in response to the indication of a clinician selection:
if it is determined that a number of doses of the substance-based orderable under a first dose option for the revised administration schedule is equal to a number of remaining doses of the substance-based orderable on the current administration schedule and when only the first dose option of the next two dose options is designated as the valid option for the revised administration schedule, and if such an equal number of doses exists, then designate the first dose option as an option for the revised administration schedule where the remaining number of doses of the substance-based orderable to be administered under the current administration schedule is maintained while observing a stop date and time for administration of the substance-based orderable that is as close as possible to the current stop date and time under the current administration schedule.

6. The system of claim 4, wherein the control server is further configured to, in response to the indication of a clinician selection:
determine another stop date and time for substance-based orderable administration under the first dose option that maintains the remaining number of doses of the substance-based orderable to be administered under the current administration schedule, thereby forming a modified first dose option;
designate the modified first dose option as an option for the revised administration schedule where the remaining number of doses of the substance-based orderable to be administered under the current administration schedule is maintained; and
based on the value of the number of doses of the substance-based orderable under the first dose option for the revised administration schedule, selectively designate the first dose option as an option for the revised administration schedule that observes a stop date and time for administration of the substance-based orderable that is as close as possible to the current stop date and time under the current administration schedule.

7. The system of claim 1, wherein the options determined account for an at least one of a future start date and time for the established order, a future stop date and time for the established order, a past start date and time for the established order, or a past stop date and time for the established order.

8. The system of claim 1, wherein the control server is further configured to communicate the options for the next administration to one or more remote computing devices.

9. A computing device comprising:
a processor configured to:
receive clinician input regarding proposed timing for changing a current administration schedule for a substance-based orderable associated with an established order;
communicate the clinician input to a remote server for updating the current administration schedule for a substance-based orderable based on the clinician input; and
receive, from the remote server, the one or more options for a revised administration schedule, wherein the one or more options at least:
maintain the administration stop date and time in the current administration schedule for the substance-based orderable independent of the number of remaining doses of the substance-based orderable, or
maintain the remaining number of doses of the substance-based orderable in the current administration schedule and maintain the administration stop date and time in the current administration schedule for the substance-based orderable; and a display component for causing concurrent presentation of two or more options via a graphical user interface (GUI), the two or more options represented graphically as selectable display objects that represent specific times for all remaining administrations of the substance-based orderable under the revised administration schedule.

10. The device of claim 9, wherein the processor is further configured to receive a clinician selection of one option of the one or more options for a revised administration schedule.

11. The device of claim 10, wherein the processor is further configured to communicate the clinician selection of the one or more options for a revised administration schedule to a remote server.

12. The device of claim 10, wherein the clinician selection of the one of the one or more options for a revised administration schedule includes more than one of a new next dose administration date and time, a new stop date and time for orderable administration, a change in the number of doses to be administered per unit-time, or a new start date and time.

13. The device of claim 10, wherein each display object presented in a context to indicate a date and time for each administration for the substance-based orderable under the respective revised administration schedule option.

14. The device of claim 10, wherein the clinician input received includes at least one of an earliest time for administering a dose and a number of doses per day of the substance-based orderable or a set of times representing when a dose of the substance-based orderable is to be administered within a day.

15. The device of claim 10, wherein the processor is further configured to update the established order associated with the substance-based orderable in an electronic order management system, wherein the updated established order uses the revised administration schedule including the one option selected by the clinician for the substance-based orderable.

* * * * *